United States Patent [19]

Wagner et al.

[11] Patent Number: 4,814,272

[45] Date of Patent: Mar. 21, 1989

[54] PROCESS FOR THE BIOTECHNICAL PRODUCTION OF RHAMNOLIPIDS INCLUDING RHAMNOLIPIDS WITH ONLY ONE β-HYDROXYDECANOIC ACID RESIDUE IN THE MOLECULE

[75] Inventors: Fritz Wagner, Stockheim; Christoph Syldatk, Hildesheim; Uwe Matulowic, Braunschweig; Hans-Jurgen Hofmann, Vechta; Kai-Udo Sewe, Barnstorf; Walter Lindorfer, Kassel, all of Fed. Rep. of Germany

[73] Assignee: Wintershall AG, Kassel, Fed. Rep. of Germany

[21] Appl. No.: 702,184

[22] Filed: Feb. 15, 1985

[30] Foreign Application Priority Data

Feb. 17, 1984 [DE] Fed. Rep. of Germany ....... 3405664

[51] Int. Cl.$^4$ .................... C07G 13/06; C12P 19/44; C12P 19/12; C12P 19/02
[52] U.S. Cl. .................................... 435/74; 435/100; 435/105; 435/249; 435/874; 536//18.2; 536/4.1
[58] Field of Search ................. 435/74, 100, 105, 178, 435/253, 247, 249, 874; 536/18.2, 4.1

[56] References Cited

FOREIGN PATENT DOCUMENTS 2150375 4/1972 Fed. Rep. of Germany .

OTHER PUBLICATIONS

Wagner, Third European Congress on Biotechnology, vol. 1 (1984), pp. I-3-I-8.
Syldatk et al., "Production of Four Interfacial Active Rhamnolipids from n-alkanes or Glycerol by Resting Cells of *Pseudomonas Species*, DSM 2874", *Z. Naturforsch*, 40c:61-67 (1985).
Wagner et al., "Production of Surface Active Anionic Glycolipids by Resting and Immobilized Microbial Cells", *Eur Congr. Biotechnol.*, 3rd, 1984 1:3-8 (Abstract).
Mandelstam et al., Part II, Chapter 2, "Growth: Cells and Populations", *Biochemistry of Bacterial Growth*, Blackwell Scientific Publications, Boston, 1982, pp. 120-122.
Chemical Abstract, vol. 86, 104438R, 1977.
Jarvis et al., J. Am. Chem. Soc., 71 (1949), pp. 4124-4126.
Itoh et al., Agr. Biol. Chem., vol. 36 (1972), pp. 2233 to 2235.
Cooper et al., Advances in Applied Microbiol,. vol. 26 (1980), pp. 229 to 253.
Bergstrom et al., Arkiv for Kemi, Mineralogi och Geologi, vol. 23A (1946), No. 13, pp. 1-12. Hisatsuka et al., Agr. Biol. Chem., vol. 5 (1971), No. 5, pp. 686-692.
Itoh et al., J. Antibiotics, vol. 24 (1971), pp. 855-859.
Cooper et al., Microbial Degradation of Pollutants in Marine Environments (1979), pp. 231-240.

*Primary Examiner*—John Tarcza
*Attorney, Agent, or Firm*—Michael N. Meller

[57] ABSTRACT

Rhamnolipids with high surface activity are produced micro iologically in high yield per g of dry cell substance using Pseudomonas spec. DSM 2874 in the form of growing, resting and immobilized cell mass in an aqueous medium containing at least one assimilable carbon source at a pH of 6.7 to 7.3 and a temperature of 30° to 37° C. Two new rhamnolipids with only one β-hydroxydecanoic acid residue in the molecule and defined as α-L-rhamnopyranosyl- and 2-O-α-L-rhamnopyranosyl-α-L-rhamnopyranosyl-β-hydroxydecanoic acid with a molecular weight of 334 and 480, respectively, are obtained.

8 Claims, No Drawings

PROCESS FOR THE BIOTECHNICAL PRODUCTION OF RHAMNOLIPIDS INCLUDING RHAMNOLIPIDS WITH ONLY ONE β-HYDROXYDECANOIC ACID RESIDUE IN THE MOLECULE

BACKGROUND OF THE INVENTION

Anionic rhamnolipids are known to be formed by growing submersed cultures of microorganisms, in particular of the genus Pseudomonas.

Thus for example in the culture of *Pseudomonas pyocyanea* in a casein/glucose medium according to the method described by Bergström et al in *Arkiv for Kemi, Mineralogi och Geologi,* Vol. 23 A (1946) No. 13, pp. 1 to 12, a "pyolipic acid" is formed which is referred to as acidic lipid.

Jarvis et al in *J. Amer. Chem. Soc.* 71 (1949), pp. 4124 to 4126 describe an anionic rhamnolipid-(I), which is designated 2-0-α-L-rhamnopyranosyl-α-L-rhamnopyranosyl-β-hydroxydecanoyl-β-hydroxydecanoic acid and accordingly has the following structural formula:

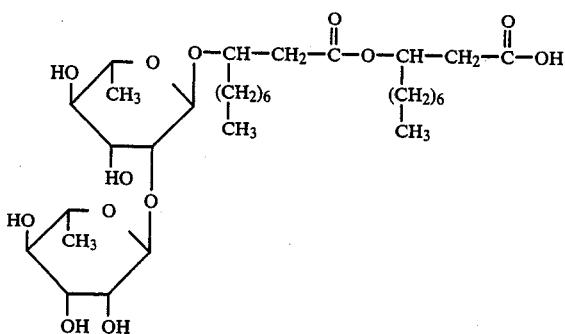

Hisatsuka et al in *Agr. Biol. Chem.,* Vol. 5 (1971), No. 5, pp. 686 to 692 describe the formation of rhamnolipids by *Pseudomonas aeruginosa* and their effect in the fermentation of hydrocarbons. These authors obtained rhamnolipid (I) with *Pseudomonas aeruginosa* using n-paraffins as carbon and energy source. This rhamnolipid (I) was found to promote the growth of *Pseudomonas aeruginosa* in an n-hexadecane medium to a very pronounced degree even in relatively small concentrations. This growth-promoting effect observed here with rhamnolipid (I) could be detected in other microorganisms which degrade hydrocarbons.

Itoh and co-workers, in their publication in *The Journ. of Antibiotics,* Vol. 24 (1971), pp. 855 to 859 take this state of the art as their starting point and state that the more precise knowledge of the biosynthesis of rhamnolipid (I) gives grounds to suppose that yet another rhamnolipid is formed which is a precursor of rhamnolipid (I). These investigators found that, from a culture of *Pseudomonas aeruginosa* growing on n-paraffin, not only the known rhamnolipid (I), which they designated rhamnolipid R-1, but also a further rhamnolipid R-2 could be isolated, which could be identified as L-α-rhamnopyranosyl-β-hydroxydecanoyl-β-hydroxydecanoate and which was recognized as a precursor of rhamnolipid (I).

These findings are also presented, using the same definitions, by Itoh et al in *Agr. Biol. Chem.,* Vol. 36 (1972), pp. 2233 to 2235. They also report that mutants of *Pseudomonas aeruginosa* which have lost the ability to use n-paraffin as nutrient grow normally on n-paraffins when rhamnolipids are added to the culture suspension. From this they conclude that the mutants have not lost the enzymatic activity which enables them to use n-paraffins as a nutrient source and that the rhamnolipids are indispensable for the degradation of n-paraffins by *Pseudomonas aeruginosa* microorganisms.

Cooper et al, in a report on rhamnolipids in *Microbial Degradation of Pollutants in Marine Environments* (1979), pp. 231 to 240, refer to the aforementioned papers and reproduce the designation of the rhamnolipid verbatim in agreement with Itoh et al loc. cit. (1971). However, for the rhamnolipid referred to as α-L-rhamnopyranosyl-β-hydroxydecanoyl-β-hydroxydecanoate these authors incorrectly state a structural formula which exhibits only one rhamnose residue and also only one hydroxydecanoic acid residue. The same error can also be found in the publication of Cooper et al in *Advances in Applied Microbiol.,* Vol. 26 (1980), pp. 229 to 253, on pp. 234 and 235.

From DE-OS No. 21 50 375, a method for the biotechnical production of rhamnose-containing glycolipids is known, in which a similar glycolipid-producing bacterium of the genus Pseudomonas is cultured aerobically in an aqueous nutrient medium containing at least one assimilable carbon source at pH levels of 4 to 10 and temperatures of 25° to 37° C. and in which the glycolipids are isolated from the nutrient broth. This process was designed to allow glycolipids to be obtained in high yields. According to the examples given in this DE-OS, the following yields are obtained with the stated Pseudomonas species on the C-base assigned to them:

| Pseudomonas species | carbon source | rhamnolipid yield in g/l culture broth |
| --- | --- | --- |
| aeruginosa ATCC 15246 | n-paraffin | 2.4 |
| fluorescens ATCC 15453 | n-paraffin | 5.0 |
| aeruginosa ATCC 10145 | glycerin | 0.87 |
| aeruginosa ATCC 10145 | n-paraffin | 9.7 |
| aeruginosa ATCC 15246 | glucose | 5.6 |
| fluorescens ATCC 15453 | glycerin | 3.3 |

As rhamnolipids, α-L-rhamnopyranosyl-β-hydroxydecanoyl-β-hydroxydecanoic acid and 2-0-L-rhamnopyranosyl-α-L-rhamnopyranosyl-β-hydroxydecanoic acid are obtained.

From this state of the art it is apparent that to date it has only been possible to produce rhamnolipids biotechnically which contain 2 hydroxydecanoic acid residues together with one or two rhamnose residues.

The object of the present invention is to discover addition rhamnolipids and means of increasing the yield of rhamnolipids relative to the cell substance.

SUMMARY OF THE INVENTION

According to the invention, a process was found by means of which rhamnolipids can be produced with the aid of microorganisms of the genus Pseudomonas in an aqueous medium, containing at least one assimilable carbon source, at pH levels above 4 and temperatures of 30° C. and above.

With this method, a Pseudomonas strain, species DSM 2874, isolated from a water sample is used as a microorganism at a pH level of 6.5 to 7.3 and a temperature of 30° to 37° C.

The Pseudomonas strain, species DSM 2874 was deposited on Feb. 3, 1983 at the International Depository, Deutsche Sammlung von Mikroorganismen, Grissbachstr. 8, D-3400 Göttingen, West Germany under No. DSM 2874.

DETAILED DESCRIPTION

The cells of this Pseudomonas strain spec. DSM 2874 are rod-shaped, have a diameter of approximately 0.5 μm and a length of about 1.0 μm are mobile and have a single flagellum. The colony of this Pseudomonas spec. DSM 2874 has a yellow coloration on the complex medium hexadecane and has a smooth colony margin with a shiny and opaque surface. The diameter of the colony is about 1 mm after one day. This strain of Pseudomonas species DSM 2874 is gram negative and aerobic, and its dry cell mass has a beige coloration. This strain liquefies gelatins and grows on glucose at a temperature of 40° C. It is also hemolysis and urease positive. This strain was also found to have the ability to degrade the following nitrogen and carbon sources:

| nitrogen sources: | ammonium sulfate | |
| --- | --- | --- |
| | sodium nitrate and nitrite | |
| | urea | |
| Carbon sources: | glucose | |
| | arabinose | glutamate |
| | fructose | serine |
| | | glycerin |
| | citrate | |
| | malonate | |
| | succinate | |
| | malate | |
| | pyruvate | glycerin |
| | | ethanol |
| | | propanol |
| | | octanol |
| | | stearic acid |
| | | myristic acid |
| | | alkanes |

The Pseudomonas strain spec. Pseudomonas spec. DSM 2874 used according to the invention also forms rhamnolipids during aerobic culture in a nutrient solution whose pH value is kept constant at 6.5 to 7.3 during culture by adding appropriate amounts of ammonium or alkali hydroxide solution, in particular sodium hydroxide solution. A nutrient solution of this type can for example contain the following substances in the stated g amounts in 1000 cm³ deionized water:

| | |
| --- | --- |
| Na$_2$HPO$_4$.2 H$_2$O | 5.34 |
| KH$_2$PO$_4$ | 2.72 |
| (NH$_4$)$_2$SO$_4$.7 H$_2$O | 8.0 |
| CaCl$_2$.2 H$_2$O | 0.2 |
| MgSO$_4$.7 H$_2$O | 0.4 |
| FeSO$_4$.7 H$_2$O | 0.02 |
| MnSO$_4$.H$_2$O | 0.0025 |
| NH$_4$—heptamolybdate | 0.001 |

The solution is first sterilized and cooled in the conventional manner before the assimilable carbon source, which has also been sterilized, is added. An n-paraffin with a content of molecules with 14 C atoms of 89% and 15 C atoms of 9% is preferably used as carbon source. Other compounds apart from those listed in the table above can naturally also be used as carbon source with goods results.

When the culture is complete, the submersed culture obtained is extracted in the usual manner with a suitable solvent such as ethyl acetate. The extracts obtained, which contain the rhamnolipids, are mixed and, preferably under vacuum, are evaporated to a residue which is finally worked up in the familiar manner, preferably by chromatography.

With a culture of this type using Pseudomonas spec. DSM 2874, the known rhamnolipids 2-0-α-L-rhamnopyranosyl-α-L-rhamnopyranosyl-β-hydroxydecanoyl-β-hydroxydecanoic acid.

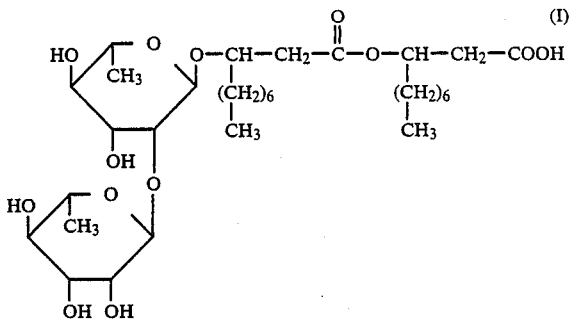

and α-L-rhamnopyranosyl-β-hydroxydecanoyl-β-hydroxydecanoic acid

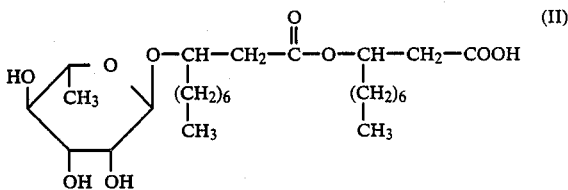

are also obtained.

The yields from the sum of these two rhamnolipids are 0.1 g per g dry cell mass and 0.8 g/1000 cm³ culture broth.

If Pseudomonas spec. DSM 2874 is cultured in the same way, but limiting the nitrogen supply, the stated rhamnolipids (I) and (II) are obtained, but in amounts of 0.5 g per g dry cell mass and about 12 g/1000 cm³ culture broth. In this case, sodium hydroxide solution is preferably used to adjust the pH value during culture.

A similar effect is achieved if Pseudomonas spec. DSM 2874 is cultured with limitation of the Mg$^{2+}$ ion concentration. The yield of rhamnolipids (I) and (II) is about 0.4 g per g dry cell mass.

The yield of rhamnolipids relative to the dry cell substance can be increased even further, if Pseudomonas spec. DSM 2874 is cultured under aerobic conditions in a nutrient solution containing an assimilable carbon source and if the wet cell substance is then separated from the culture broth. Rhamnolipids can be isolated—as described above—from the liquid phase remaining after this separation.

The wet cell mass (resting cells) obtained is, if necessary—also after intermediate storage at a temperature of −30° to −35° C.—suspended in a dilute sodium chloride solution containing 0.4 to 0.6% by weight NaCl. After addition of an assimilable carbon source such as glycerin or n-paraffin (89% C$_{14}$ and 9% C$_{15}$), this suspension is incubated with vigorous shaking at a temperature of about 30° to 40° C., the pH value of the suspension being continuously monitored and maintained at a level between 6.0 and 6.8 by addition of appropriate amounts of 1N sodium hydroxide solution. When the incubation is completed, the wet cell mass is separated. The pH value of the aqueous supernatant is lowered to about 2 with a dilute, preferably, 10% solution of a strong mineral acid such as sulfuric acid or hydrochloric acid, and from this the rhamnolipids are then isolated. The wet cell mass is suspended once more in sodium chloride solution and then incubated in the same manner as described above after addition of an assimilable carbon source. These operations can be repeated once again with the resting cells. The production activity of these resting cells is then virtually zero.

In the first application of the resting cells, a yield of about 1.1 g rhamnolipids per g dry cell mass is obtained, on the second application 32% and on the third application still 14% of this quantity of rhamnolipids are obtained as yield, which represents a total yield of about 1.6 g rhamnolipids per g dry cell mass.

Using this process, rhamnolipids were isolated for the first time which contain only one $\beta$-hydroxydecanoyl residue in the molecule and which have molecular weights of 334 and 480. These rhamnolipids have the structural formulae

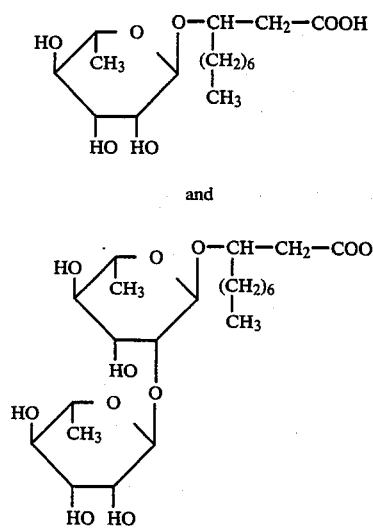

and can be designated $\alpha$-L-rhamnopyranosyl-$\beta$-hydroxydecanoic acid (rhamnolipid (III) and 2-0-$\alpha$-L-rhamnopyranosyl-$\alpha$-L-rhamnopyranosyl-$\beta$-hydroxydecanoic acid (rhamnolipid (IV)). These structures have been definitively elucidated with the aid of elementary analysis $^{13}$C- and $^1$H nuclear resonance spectroscopy and mass spectroscopy.

It has also been established that the composition of the mixtures of rhamnolipids (I) to (IV) produced with resting cells is dependent on the assimilable carbon source and, if the same carbon source is used, on the incubation temperature, as is shown by the following tables:

TABLE 1

Dependence of the composition of a mixture of rhamnolipids (I) to (IV) produced with resting cells at an incubation temperature of 30° C. on the type of the assimilable carbon source

| Rhamnolipid | glycerin | n-paraffin (89% $C_{14}$, 9% $C_{15}$) |
|---|---|---|
| (I) | 61.5% | 41% |
| (II) | 22.4% | 42% |
| (III) | 15.1% | 15% |
| (IV) | 1.0% | 2% |

TABLE 2

Dependence of the composition of a mixture of rhamnolipids (I) to (IV) produced with resting cells with the same carbon source n-paraffin (89% $C_{14}$, 9% $C_{15}$) on the incubation temperature.

| rhamnolipid | 30° C. | 37° C. |
|---|---|---|
| (I) | 41% | 32% |
| (II) | 42% | 66% |
| (III) | 15% | 1% |
| (IV) | 2% | 1% |

Another possibility of obtaining rhamnolipids in good yields with Pseudomonas spec. DSM 2874 is offered by a further variant of the process according to the invention. With this variant, Pseudomonas spec. DSM 2874 is cultured aerobically in a nutrient solution containing an assimilable carbon source such as glucose, n-paraffin or the like, preferably at a temperature of 30° to 37° C., with the pH value in the culture broth being kept constant, preferably at 6.8 to 7.2, by addition of appropriate amounts of dilute, preferably 10% sodium hydroxide solution. When the incubation is complete, the wet cell mass is separated from the culture broth and suspended in a dilute, preferably 0.5 to 1.0% sodium chloride solution, and a sodium alginate solution is then stirred into this suspension. This mixture while being stirred is then added dropwise to an unsaturated calcium chloride solution and is then further stirred until granules have formed which have an average diameter of about 1.5 mm. These granules are separated from the liquid phase and transferred to an unsaturated sodium chloride solution, preferably containing 0.5 to 1.0% by weight NaCl, and which contains small amounts of calcium chloride in solution and an assimilable carbon source such as glycerin, n-paraffin (89% $C_{14}$, 9% $C_{15}$) or the like. After the incubation, which is performed at a temperature of 30° to 40° C. and a pH level of 6.5 to 6.9, the granules are separated from the liquid phase, from which the rhamnolipids are isolated by extraction. The separated granules can still be used several times as a biocatalyst in the same manner. They lose their activity much more slowly than the resting cells mentioned above. The relative activity of the granules—assuming a value of 100% for the first application—is 90% in the second application, 44% in the third and still 34% in the fourth application.

Rhamnolipids (I) to (IV) are also obtained with the cell mass of Pseudomonas spec. DSM 2874 immobilized in the form of granules.

The rhamnolipids produced according to the invention, as well as their mixtures, are distinguished by excellent interface-active properties which show no temperature dependency in the n-hexadecane/water system in a temperature range of 20° to 90° C., and are affected as little by changes in pH value within the range 3 to 9 as by salinity of the aqueous phase in the range between >0 and 14% by weight. Hydrolysis of the rhamnolipids was also not detected within these ranges.

For these reasons, the rhamnolipids produced according to the invention are outstandingly suitable as interface-active additives for tertiary flooding of petroleum deposits. Experiments have demonstrated that oil removal increases of more than 12% can be achieved with an addition of rhamnolipids of only 0.5 to 0.7 g/l flood water.

EXAMPLE 1

Formation of rhamnolipids with growing cells

Culture of Pseudomonas species DSM 2874 is performed at 100 rpm and pH of 6.8 in 500 ml Erlenmeyer flasks with baffles, each containing 100 ml culture medium (composition: 0.534 g $Na_2HPO_4.2\ H_2O$, 0.272 g $KH_2PO_4$, 0.8 g $(NH_2)_2SO_4.7\ H_2O$, 0.02 g $CaCl_2.2\ H_2O$, 0.04 g $MgSO_4$, 0.002 g $FeSO_4.7\ H_2O$, 0.00025 g $MnSO_4 \cdot H_2O$, 0.0001 g $NH_4$ heptamolybdate and 100 ml dist. water) which is sterilized for 30 minutes at 121° C., compounded after cooling to 30° C. with 2 g sterile paraffin S (89% $C_{14}$, 9% $C_{15}$) and inoculated with 1 ml of a 24 hour old submersed culture of Pseudomonas spec. DSM 2874. During culture, the pH value of the submersed culture is corrected to pH 6.8 after 24 h and 48 h with sterile 1N NaOH solution. Culturing is complete after 72 hr, after which the submersed cultures obtained are exhaustively extracted with ethyl acetate in the conventional manner. After concentration under vacuum, the organic extracts contain 80 mg rhamnolipids, specifically 40 mg rhamnolipid I=50% relative to total rhamnolipid, and 40 mg rhamnolipid II=50% relative to total rhamnolipid.

EXAMPLE 2

Formation of rhamnolipids with growing cells with limitation of the $Mg^{2+}$ ions As in Example I, Pseudomonas species DSM 2874 is cultured, but instead of 0.04 g, only 0.002 g $MgSO_4.7\ H_2O$ is contained in the culture medium. The extraction is performed as described in Example 1. The organic extracts obtained contain 113 mg rhamnolipid II=65% relative to total rhamnolipid and 60 mg rhamnolipid I=35% relative to total rhamnolipid.

EXAMPLE 3

Formation of rhamnolipids with growing cells with nitrogen limitation

A bioreactor equipped with a recycling system is compounded with 20 l nutrient salt solution (composition: 6 g citrate-1-hydrate, 88.4 g $Na_2HPO_4.2\ H_2O$, 68 g $KH_2PO_4$, 160 g $(NH_4)_2SO_4$, 12 g $CaCl_2.2\ H_2O$, 12 g $MgSO_4$ 0.036 g $NH_4$ heptamolybdate and 20 l deionized water), sterilize phosphate separately in 1000 ml deionized $H_2O$ and add only after sterilization, sterilized for 30 min at pH 3.0 and 121° C., and compounded after cooling to 30° C. with 1,600 g sterile paraffin S (89% $C_{14}$, 9% $C_{15}$). The pH value of the culture solution is adjusted to pH 6.6 with 10% $NH_4OH$ solution and inoculated with 2000 ml of a 24-hour old submersed culture of Pseudomonas spec. DSM 2874. During culture, the submersed culture is kept constant at pH values between 6.6 and 7.2 automatically with the aid of a pH regulating station, initially by titration with 800 ml of a 10% NaOH solution and, following this, by titration with a 10% NaOH solution and is then aerated with air at 30° C., a rotational speed of 1000 rpm and an aeration rate of 0.6 V/V/m. Culturing is completed after 168 hours, after which the submersed culture is exhaustively extracted with ethyl acetate in the usual manner. The combined organic extracts are concentrated under vacuum, the crude organic extract contains in addition to paraffin S (200 g), which is recycled, 156 g rhamnolipid II=65% relative to total rhamnolipid and 83 g rhamnolipid I=35% relative to total rhamnolipid.

EXAMPLE 4

Culture of Pseudomonas species DSM 2874

A bioreactor equipped with a recycling system is compounded with 22 l of a nutrient salt solution (composition: 5 g citrate-1-hydrate, 110 g $Na_2HPO_4.2\ H_2O$, 85 g $KH_2PO_4$, 152.5 g $(NH_4)_2SO_4$, 10 g $CaCl_2.2\ H_2O$, 10 g $MgSO_4.7\ H_2O$, 1 g $FeSO_4.7\ H_2O$, 0.125 g $MnSO_4 \cdot H_2O$ and 0.03 g $NH_4$ heptamolybdate and 22 l deionized water), sterilized for 30 min at pH 3.0 and 121° C., compounded after cooling to 30° C. with 1000 g of 50% by weight sterile glucose solution, the pH value adjusted to pH 6.8 with 10% NaOH solution and inoculated with 2500 ml of a 24-hour old submersed culture of Pseudomonas species DSM 2874. During culture, the submersed culture is kept at a constant pH level between 6.8 and 7.2 with the aid of a pH regulating station and titration with a 10% NaOH solution, and is aerated with air at 30° C., a rotational speed of 1500 rpm at an aeration rate of 0.62 V/V/m. The glucose is consumed after 9 hours, after which the cell mass is separated from the culture suspension by centrifugation in the familiar manner. 0.92 kg wet cell mass is obtained and stored at −32° C.

EXAMPLE 5

Formation of rhamnolipids with resting cells 2.0 g of the wet cell mass obtained according to Example 4 are suspended in 100 ml of 0.5% by weight NaCl solution, compounded with 4 g glycerin and this suspension is then incubated at 30° C. and 100 rpm in a 500 ml Erlenmeyer flask on a rotary shaker. The pH value is corrected to pH 6.6 with 1N NaOH solution. After an incubation time of 168 hours, the suspension is adjusted to pH 2.0 with 10% by weight of $H_2SO_4$ and exhaustively extracted with ethyl acetate. The combined organic extracts are concentrated under vacuum. The crude organic extract contains:
430.0 mg rhamnolipid (I) representing 61.5%
156.8 mg rhamnolipid (II) representing 22.4%
105.7 mg rhamnolipid (III) representing 15.1% and
7 mg rhamnolipid (IV) representing 1%.
The percentage data signify the percentage proportion of the individual rhamnolipid in the total rhamnolipid quantity obtained.

EXAMPLE 6

Formation of rhamnolipids with resting cells 2.0 g of the wet cell mass obtained according to Example 4 are suspended in 100 ml of 0.5% by weight of NaCl solution, compounded with 4 g of n-paraffin (89% $C_{14}$, 9% $C_{15}$) and incubated and extracted as described in Example 5. The crude organic extract contains:
639.6 mg rhamnolipid (I) representing 41%
655.2 mg rhamnolipid (II) representing 42%
234 mg rhamnolipid (III) representing 15%
31.2 mg rhamnolipid (IV) representing 2%
in each case relative to the total amount of the yield of rhamnolipids.

EXAMPLE 7

Formation of rhamnolipids with resting cells 2.0 g of the wet cell mass obtained according to Example 4 are suspended in 100 ml of 0.5% by weight NaCl solution, compounded with 4 g of n-paraffin (89% $C_{14}$, 9% $C_{15}$) and, as described in Example 5, incubated—but at 37° C.—and then extracted. The crude organic extract contains 450 mg rhamnolipid I=62% relative to total rhamnolipid and 270 mg rhamnolipid II=37% relative to total rhamnolipid. Rhamnolipids III and IV are <1% relative to total rhamnolipid.

EXAMPLE 8

Formation of rhamnolipids with immobilized cells 40 g of the wet cell mass obtained according to Example 4 are suspended in 40 ml of 0.9% by weight NaCl solution and this suspension is transferred while being stirred to 360 ml of an aqueous 3% by weight Na-alginate solution. The suspension thus obtained is added dropwise while being stirred to 600 ml of 2% by weight $CaCl_2$ solution. The ionotropic interconversion is concluded after 40 min and the granules with a mean diameter of 1.5 mm are filtered off. The immobilized cells obtained in this manner are incubated for 70 hours at 30° C. and pH 6.8 in 1000 ml of an aqueous solution which contains 2% by weight glycerin, 0.25% by weight NaCl and 0.037% by weight $CaCl_2$. The immobilized cells are filtered off and can be used again as a biocatalyst. The aqueous filtrate is extracted as described in Example 5. The crude organic extract contains 1830 mg rhamnolipid I=61% relative to total rhamnolipid, 630 mg rhamnolipid II=21% relative to total rhamnolipid, 480 mg rhamnolipid III=16% relative to total rhamnolipid and 60 mg rhamnolipid IV=2% relative to total rhamnolipid.

We claim:

1. A process for the microbiological production of rhamnolipids comprising the following steps:
   (a) culturing the microorganism Pseudomonas species DSM 2874 under aerobic conditions in an aqueous nutrient solution containing at least one assimilable carbon source at a pH value of 6.5 to 7.3 and a temperature of 30° to 37° C., then either
   (b) extracting the aqueous culture directly with a suitable solvent and evaporating the extract or else
   (c) separating the resulting aqueous wet cell mass of resting cells from the culture broth and suspending said wet cell mass in a dilute sodium chloride solution and, after addition of an assimilable carbon source, incubating the resting cell suspension at a temperature of 30° to 40° C. at a constant pH of 6.0 to 6.9, then adjusting the pH value of the suspension to about 2.0 with a dilute solution of a strong mineral acid and isolating the rhamnolipids from said acid solution by extraction with a suitable solvent and evaporation of the extract.

2. The process according to claim 1, wherein the Pseudomonas species DSM 2874 is cultured under aerobic conditions in a nutrient solution which contains one assimilable carbon source and is limited in its nitrogen content and wherein the rhamnolipids are subsequently isolated from the culture.

3. The process according to claim 1, wherein the Pseudomonas species DSM 2874 is cultured under aerobic conditions in a nutrient solution which contains one assimilable carbon source and is limited in its content of $Mg^{2+}$ ions and wherein the rhamnolipids are subsequently isolated from the culture.

4. The process according to claim 1, wherein the wet cell mass separated from the culture broth is stored at temperatures of −30° to −35° C. before being suspended in the dilute sodium chloride solution.

5. The process according to claim 1, wherein after incubating, the wet cell mass is separated from the liquid phase from the suspension of the wet cell mass in sodium chloride solution and is suspended and incubated in sodium chloride solution once again and in the same manner, with the rhamnolipids being isolated from the liquid phase.

6. The process according to claim 1, wherein the Pseudomonas species DSM 2874 is cultured under aerobic conditions in a nutrient solution containing one assimilable carbon source and further comprising the steps of separating a wet cell mass from the culture broth, suspending said wet cell mass in a dilute sodium chloride solution, stirring a sodium alginate solution into the suspension, adding the suspension, while being stirred, dropwise to an unsaturated calcium chloride solution, continuing the stirring until granules have formed, separating the granules from the liquid phase, incubating the granules in an unsaturated sodium chloride solution containing small amounts of calcium chloride and one assimilable carbon source at a temperature of 30° to 40° C. while maintaining a pH level of 6.5 to 6.9, separating the granules from the liquid phase, and isolating the rhamnolipids from the liquid phase.

7. The process according to claim 6, wherein the granules separated from the liquid phase after the incubation are incubated once again.

8. A rhamnolipid selected from the group consisting of α-L-rhamnopyranosyl-β-hydroxydecanoic acid and 2-O-α-L-rhamnopyranosyl-α-L-rhamnopyranosyl-β-hydroxydecanoic acid.

* * * * *